United States Patent [19]

Drenski et al.

[11] Patent Number: 5,770,757
[45] Date of Patent: Jun. 23, 1998

[54] AMMOXIDATION CATALYSTS CONTAINING GERMANIUM TO PRODUCE HIGH YIELDS OF ACRYLONITRILE

[75] Inventors: Tama Lee Drenski, Twinsburg; Maria Strada Friedrich, Lyndhurst; Christos Paparizos, Willowick; Michael J. Seely, Twinsburg; Dev Dhanaraj Suresh, Hudson, all of Ohio

[73] Assignee: The Standard Oil Company, Cleveland, Ohio

[21] Appl. No.: 646,742

[22] Filed: May 3, 1996

Related U.S. Application Data

[63] Continuation-in-part of Ser. No. 461,996, Jun. 5, 1995, abandoned.

[51] Int. Cl.⁶ .................. C07C 255/08; C07C 253/12
[52] U.S. Cl. ................................. 558/300; 558/319
[58] Field of Search .................................. 558/319, 300

[56] References Cited

U.S. PATENT DOCUMENTS

| | | | |
|---|---|---|---|
| 4,001,317 | 1/1977 | Grasselli et al. | 260/533 |
| 4,155,938 | 5/1979 | Yamamoto et al. | 260/604 |
| 4,162,234 | 7/1979 | Grasselli et al. | 252/432 |
| 4,190,556 | 2/1980 | Grasselli et al. | 252/432 |
| 4,495,109 | 1/1985 | Grasselli et al. | 260/465.3 |
| 4,816,603 | 3/1989 | Oh-Kita et al. | 562/538 |
| 5,079,207 | 1/1992 | Brazdil et al. | 502/205 |
| 5,093,521 | 3/1992 | Oh-Kita et al. | 562/534 |
| 5,102,847 | 4/1992 | Yamamoto et al. | 502/205 |
| 5,134,105 | 7/1992 | Paparizos et al. | 502/205 |
| 5,183,793 | 2/1993 | Paparizos et al. | 502/338 |

OTHER PUBLICATIONS

The Condensed Chemical Dictionary, 10th Ed., Revised by Gessner G. Hawley (Van Nostrand Reinhold Co.) 1981, pp. 883–884.

*Primary Examiner*—Johann Richter
*Assistant Examiner*—Ebenezer Sackey
*Attorney, Agent, or Firm*—Michael F. Esposito; David P. Yusko; David J. Untener

[57] ABSTRACT

A catalyst having the atomic ratios set forth in the empirical formula below:

$$A_aB_bC_cGe_dBi_eMo_{12}O_x$$

where
  A=two or more of alkali metals, In and Tl
  B=one or more of Mg, Mn, Ni, Co, Ca, Fe, Ce, Sm, Cr, Sb, and W; preferably B equals the combination of Fe and at least one element selected from the group consisting of Ni and Co and at least one element selected from the group consisting of Mg, Mn, Ca, Ce, Sn, Cr, Sb, and W
  C=one or more of Pb, Eu, B, Sn, Te and Cu
  a=0.05 to 5.0
  b=5 to 12
  c=0 to 5.0
  d=0.1 to 2.0
  e=0.1 to 2.0
  x=the number of oxygen atoms required to satisfy the valency requirements of the other elements and
  b>a+c.

8 Claims, No Drawings

AMMOXIDATION CATALYSTS CONTAINING GERMANIUM TO PRODUCE HIGH YIELDS OF ACRYLONITRILE

This application is a continuation-in-part of U.S. Ser. No. 08/461,996 filed Jun. 5, 1995, now abandoned.

BACKGROUND OF THE INVENTION

1. Field of the Invention

The present invention is directed to an improved ammoxidation catalyst for use in the manufacture of acrylonitrile. In particular, the present invention is directed to an improved ammoxidation catalyst containing germanium as an essential element and a combination of at least two alkali metals for the production of acrylonitrile by the ammoxidation of propylene.

The ammoxidation of propylene to acrylonitrile using a fluid bed catalyst is a well known commercial process referred to in the industry as the Sohio Acrylonitrile Process. The process comprises contacting propylene over a catalyst in a fluid bed reactor at an elevated temperature in the presence of ammonia and air. High yields of acrylonitrile have been obtained utilizing this process.

A number of very desirable ammoxidation catalysts are known which represent the base catalyst utilized in the practice of the present invention. These catalysts have been used not only to produce acrylonitrile but also methacrylonitrile. Examples of patents which disclose catalysts suitable for the ammoxidation of propylene to acrylonitrile in a fluid bed reactor include U.S. Pat. Nos. 4,190,556; 4,162,234; 4,001,317; 4,001,317 and 5,093,299. Each of these patents is assigned to the assignee of the instant application.

While current commercial catalysts produce desirable results in the commercial production of acrylonitrile, improvement is always being sought. The present invention is directed to an improved ammoxidation catalyst containing at least two alkali metals and germanium as an essential element for the production of acrylonitrile.

SUMMARY OF THE INVENTION

It is an object of the present invention to provide an ammoxidation catalyst useful in the manufacture of acrylonitrile.

It is another object of the present invention to provide a novel process for the manufacture of acrylonitrile utilizing a fluid bed ammoxidation catalyst.

It is still another object of the present invention to provide a novel method of preparing an ammoxidation catalyst useful for the production of acrylonitrile.

Additional objects and advantages of the invention are set forth in part in the description which follows and, in part will be obvious from the description or may be learned by the practice of the invention. The objects and advantages of the invention may be realized and attained by means of the instrumentalities and combinations particularly pointed out in the appended claims.

To achieve the foregoing objects and advantages as set forth above, the catalyst of the present invention has the atomic ratios described by the empirical formula set forth below:

$$A_a B_b C_c Ge_d Bi_e Mo_{12} O_x$$

where
A=two or more of alkali metals, In and Tl, preferably Li, K and Cs

B=one or more of Mg, Mn, Ni, Co, Ca, Fe, Ce, Sm, Cr, Sb, and W; preferably B equals the combination of Fe and at least one element selected from the group consisting of Ni and Co and at least one element selected from the group consisting of Mg, Mn, Ca, Ce, Sn, Cr, Sb, and W C=one or more of Pb, Eu, B, Sn, Te and Cu;
a=0.05 to 5.0
b=5 to 12
c=0 to 5.0
d=0.1 to 2.0
e=0.1 to 2.0
x=the number of oxygen required to satisfy the valency requirements of the other elements present, and
b>a+c.

It is also an additional object of the present invention to provide a process for the preparation of acrylonitrile or methacrylonitrile by the reaction of propylene or isobutylene, molecular oxygen and ammonia at a temperature of between 200° C. to about 600° C. in the presence of a catalyst, the improvement comprising using a catalyst having the atomic ratios described by the empirical formula set forth below:

$$A_a B_b C_c Ge_d Bi_e Mo_{12} O_x$$

where
A=two or more of alkali metals, In and Tl, preferably Li, K and Cs

B=one or more of Mg, Mn, Ni, Co, Ca, Fe, Ce, Sm, Cr, Sb, and W; preferably B equals the combination of Fe and at least one element selected from the group consisting of Ni and Co and at least one element selected from the group consisting of Mg, Mn, Ca, Ce, Sn, Cr, Sb, and W C=one or more of Pb, Eu, B, Sn, Te and Cu;
a=0.05 to 5.0
b=5 to 12
c=0 to 5.0
d=0.1 to 2.0
e=0.1 to 2.0
x=the number of oxygen required to satisfy the valency requirements of the other elements present, and
b>a+c.

In a preferred embodiment of the present invention the catalyst is supported on inert supports selected from the group consisting of silica, alumina, zirconia and mixtures thereof. Most preferably the support is silica. Typically, the level of the support is usually in the range of 20 to 70 weight percent, preferably the range of the support is between 40 to 60 weight percent.

The catalysts of the present invention are prepared by conventional procedures taught in the prior art. However, it has been discovered that once the catalyst ingredients have been mixed typically in the form of metal nitrate solutions and ammonium hepta-molybdate that the catalyst performance may be improved by certain calcination procedures. Accordingly, it is a further object of the present invention to provide a procedure for treating the catalyst precursor comprising an aqueous mixture of the metal nitrates and ammonia hepta-molybdate as follows: the catalyst precursor is dried at a temperature of 50° to 300° C. in a hot chamber, the temperature is then increased to a temperature of 200° to 500° C. to remove the nitrates from the catalyst precursor, finally, the catalyst precursor is calcined at a temperature of between 450° to 750° C. to produce the resulting catalyst.

Typically, the heat treatment can be done in a reducing environment such as ammonia, carbon, carbon monoxide, nitrous oxide, or an inert environment such as nitrogen, carbon dioxide, steam, etc., or in an oxidizing environment such as air, oxygen, nitrogen dioxide, etc., and their combinations. The nitrogen oxide evolved during the denitrification can also be passed over the catalyst to improve the calcination of the catalyst at various stages of the heat treatment.

In a preferred embodiment of the present invention, the amount of A element present in the catalyst may range from a=0.05 to 2, preferably 0.1 to 2.

In another preferred embodiment of the present invention, the amount of B element may range from b=6 to 12, preferably 8 to 12.

In still another embodiment of the present invention, c varies from 0.1 to 2.

In a further preferred embodiment of the present invention, B equals the combination of Fe and Ni plus at least one element selected from the group consisting of Mg, Mn, Ca, Ce, Sn, Cr, Sb, and W.

In another preferred embodiment of the present invention, B equals the combination of Fe plus at least one element selected from the group consisting of Ni and Co plus at least one element selected from the group consisting of Mg, Mn, Ca, Ce, Sb, and W.

In still another embodiment of the present invention, B equals the combination of Fe plus Ni plus at least one element selected from the group consisting of Mg, Mn, Ca, Ce, Sb, and W.

In a still further preferred embodiment of the present invention, the catalyst is substantially free of phosphorus.

The reactants, process conditions and other reaction parameters of the reaction are known in the art of ammoxidation of propylene and isobutylene. The conditions, reactors and the like are not substantially changed from those disclosed in the art. The temperatures may range from about 200° to 600° C. with about 300° to 500° C. being preferred. The reaction may be conducted in a fluid or fixed bed reactor using atmospheric, sub-atmospheric or super-atmospheric pressures. Preferably, the reaction is conducted in a fluid bed reactor at atmospheric pressures. The reactant feed rate is normally stated as "WWH" and is measured according to the following formula: WWH=weight of olefin fed/weight of catalyst times hours. Typically, the WWH ranges from between 0.05 to about 0.25. The following examples are illustrative of the claimed invention and are supplied for purposes of illustration only.

SPECIFIC EXAMPLES

Catalysts containing germanium and catalysts without germanium were prepared in fluid bed form. All these catalysts contain 40 weight percent $SiO_2$. The inlet of the spray drier was 325° C., and the outlet temperature was 145° C. The catalyst was de-nitrified at 290° C. for a period of 3 hours followed by 425° C. for 3 hours. Final calcination was done in air at 540°–590° C. for 3 hours. The microspheroidal catalyst was placed in a 40 cc fluid bed reactor, and a feed containing a mixture of $NH_3$ and $N_2$ was passed over the catalyst at ~440° C. for a period of 10 minutes. The feed was then changed to a gas mixture containing propylene, ammonia, oxygen and nitrogen, and the temperature of the reactor was lowered to 410°–420° C. Recovery runs were made after the catalyst had been on this feed gas for about 20 hours. The following examples clearly show the advantage of germanium in the molybdate based catalysts:

TABLE I

| Ex. No. | Composition of Catalysts | % AN Yield |
| --- | --- | --- |
| 1 (Comparative) | $Li_{0.25}Cs_{0.1}K_{0.1}Ni_{6.2}Mg_{2.5}Fe_2Bi_{0.75}Ce_{0.5}Mo_{14.0}O_x$ | 82.2 |
| 2 | $Li_{0.25}Cs_{0.1}K_{0.1}Ni_{6.2}Mg_{2.5}Fe_2Bi_{0.75}Ce_{0.5}Mo_{14.0}Ge_{0.5}O_x$ | 82.5 |
| 3 (Comparative) | $Li_{0.25}Cs_{0.1}K_{0.1}Ni_{6.2}Mg_{2.5}Fe_2Bi_{0.5}Ce_{0.5}Mo_{13.6}O_x$ | 82.1 |
| 4 | $Li_{0.25}Cs_{0.1}K_{0.1}Ni_{6.2}Mg_{2.5}Fe_2Bi_{0.5}Ce_{0.5}Mo_{13.6}Ge_{0.5}O_x$ | 82.6 |
| 5 (Comparative) | *$Cs_{0.1}K_{0.1}Ni_{6.2}Mg_{2.5}Fe_2Bi_{0.5}Ce_{0.5}Mo_{13.6}O_x$ | 81.5 |
| 6 | $Cs_{0.1}K_{0.1}Ni_{6.2}Mg_{2.5}Fe_2Bi_{0.5}Ce_{0.5}Mo_{13.6}Ge_{0.5}O_x$ | 82.4 |
| 7 | $Ge_{0.5}Li_{0.5}Cs_{0.1}K_{0.1}Ni_{8.7}Mg_0Fe_2Bi_{0.75}Ce_{0.5}Mo_{13.6}O_x$ | 82.7 |
| 8 | $Ge_{0.5}Li_{0.5}Cs_{0.1}K_{0.1}Ni_{6.2}Mg_{2.5}Fe_2Bi_{0.75}Ce_{0.5}Mo_{13.6}O_x$ | 82.5 |
| 9 | $Ge_{0.5}Cs_{0.1}K_{0.1}Ni_{6.2}Mg_{2.5}Fe_2Bi_{0.75}Ce_{0.5}Mo_{14.0}O_x$ | 82.3 |

*Catalyst contains 50% $SiO_2$ support

Several fixed bed catalysts, supported with 40 weight percent $SiO_2$, were prepared with and without germanium. These catalysts were dried in a drying oven at ~130° C. for ~24 hours followed by 290° C. heat treatment for 3 hours and 425° C. heat treatment for 3 hours. The catalyst was then broken into 20 to 35 mesh particles and further calcined at 550°–600° C. for a period of 3 hours. The catalyst was then placed in 5 cc microreactor at ~430° C. and evaluated for the ammoxidation of propylene to acrylonitrile by feeding a gas mixture containing propylene, ammonia oxygen, nitrogen and water. All catalysts were tested under identical conditions. The following examples will show the distinct advantage of adding germanium to the molybdate based catalysts.

TABLE II

| Ex. No. | Fixed Bed Catalyst | % AN Yield |
| --- | --- | --- |
| 10 (Comparative) | $Cs_{0.1}K_{0.1}Ni_{6.2}Mg_{2.5}Fe_2Bi_{0.5}Ce_{0.5}Mo_{13.6}O_x$ | 82.7 |
| 11 | $Cs_{0.1}K_{0.1}Ni_{6.2}Mg_{2.5}Fe_2Bi_{0.5}Ce_{0.5}Mo_{13.6}Ge_{0.5}O_x$ | 84.4 |
| 12 | $Cs_{0.1}K_{0.1}Ni_{6.2}Mg_{2.5}Fe_2Bi_{0.5}Ce_{0.5}Mo_{13.6}Ge_{0.5}O_{x(Ge\ to\ AHM)}$ | 84.2 |
| 13 | $Cs_{0.1}K_{0.1}Ni_{8.7}Fe_2Bi_{0.5}Ce_{0.5}Mo_{13.6}Ge_{0.5}O_x$ | 82.7 |
| 14 | $Cs_{0.1}K_{0.1}Ni_{6.2}Mg_{2.5}Fe_2Bi_{0.75}Ce_{0.5}Mo_{14.0}Ge_{0.5}O_x$ | 83.6 |

TABLE II-continued

| Ex. No. | Fixed Bed Catalyst | % AN Yield |
|---|---|---|
| 15 | $Cs_{0.1}K_{0.1}Ni_{6.2}Mg_{2.5}Fe_2Bi_{0.5}Ce_{0.5}Mo_{12.8}Ge_{0.5}O_x$ | 82.0 |
| 16 | $Cs_{0.1}K_{0.1}Ni_{6.2}Mg_{2.5}Fe_2Bi_{0.5}Ce_{0.5}Mo_{13.2}Ge_{0.5}W_{0.4}O_x$ | 83.8 |
| 17 | $Cs_{0.1}K_{0.1}Ni_{6.2}Mg_{2.5}Fe_2Bi_{0.5}Ce_{0.5}Mo_{14.1}Ge_{0.75}O_x$ | 84.0 |
| 18 (Comparative) | *$Cs_{0.1}K_{0.1}Ni_{6.2}Mg_{2.5}Fe_2Bi_{0.5}Ce_{0.5}Mo_{13.6}O_x$ | 82.1 |
| 19 | *$Cs_{0.1}K_{0.1}Ni_{6.2}Mg_{2.5}Fe_2Bi_{0.5}Ce_{0.5}Mo_{13.6}Ge_{0.5}O_x$ | 82.9 |
| 20 (Comparative) | *$Cs_{0.1}K_{0.1}Ni_{5.5}Mg_{2.2}Fe_2Mn_1Bi_{0.5}Cr_{0.5}Mn_{12.3}O_x$ | 82.0 |
| 21 | *$Cs_{0.1}K_{0.1}Ni_{5.5}Mg_{2.2}Fe_2Mn_1Bi_{0.5}Cr_{0.5}Mo_{13.6}Ge_{0.5}O_x$ | 84.4 |
| 22 | *$Cs_{0.1}K_{0.1}Ni_{6.2}Mg_{2.5}Fe_2Bi_{0.75}Cr_{0.5}Mo_{13.6}Ge_{0.5}O_x$ | 85.3 |
| 23 | *$Cs_{0.1}K_{0.1}Ni_{6.2}Mg_{2.5}Fe_2Bi_{0.5}Ce_{0.25}Mo_{13.6}Ge_{0.25}O_x$ | 83.9 |
| 24 | *$Cs_{0.1}K_{0.1}Ni_{6.2}Mg_{2.5}Fe_2Bi_{0.875}Ce_{0.5}Mo_{13.6}Ge_{0.5}O_x$ | 82.6 |
| 25 | *$Cs_{0.1}K_{0.1}Ni_{8.7}Fe_2Bi_{1.0}Ce_{0.5}Mo_{14.4}Ge_{0.5}O_x$ | 84.8 |
| 26 | *$Cs_{0.1}K_{0.1}Ni_{8.8}Fe_2Bi_{1.75}Ce_{0.5}Mo_{14.1}Ge_{0.5}O_x$ | 83.7 |
| 27 | *$Cs_{0.1}K_{0.1}Ni_{8.7}Fe_2Bi_{0.5}Ce_{0.5}Mo_{13.6}Ge_{0.5}O_x$ | 83.7 |

*Contains 50 wt % $SiO_2$

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as our invention is:

1. A process for the preparation of acrylonitrile or methacrylonitrile by the reaction of propylene or isobutylene, molecular oxygen and ammonia at a temperature of between 200° C. to about 600° C. in the presence of a catalyst, the improvement comprising using a catalyst having the atomic ratios described by the empirical formula set forth below:

where

A=two or more of alkali metals, In and Tl

B=the combination of Fe plus at least one element selected from the group consisting of Ni and Co plus at least one element selected from the group consisting of Mg, Mn, Ca, Ce, Sn, Cr, Sb, and W C=one or more of Pb, Eu, B, Sn, Te and Cu a=0.05 to 5.0 b=5 to 12 c=0 to 5.0 d=0.1 to 2.0 e=0.1 to 2.0 x=the number of oxygen atoms required to satisfy the valency requirements of the other elements and b>a+c.

2. The process of claim 1 wherein a ranges from 0.1 to 2.

3. The process of claim 1 wherein B equals the combination of Fe plus Ni and at least one element selected from the group consisting of Mg, Mn, Ca, Ce, Sn, Cr, Sb, and W.

4. The process of claim 1 wherein c ranges from 0.1 to 2.

5. The process of claim 1 wherein the catalyst is further comprising supported on an inert support.

6. The process of claim 5 wherein the inert support is selected from the group consisting of silica, zirconia, and alumina or mixtures thereof.

7. The process of claim 6 wherein the inert support is present in the range of 20 to 70 weight percent.

8. The process of claim 7 wherein the inert support is present in the range of 40 to 60 weight percent.

* * * * *